(12) United States Patent
Wang et al.

(10) Patent No.: US 6,562,061 B1
(45) Date of Patent: May 13, 2003

(54) STENT DELIVERY BALLOON WITH SECUREMENT STRUCTURE

(75) Inventors: Lixiao Wang, Maple Grove, MN (US); John Jianhua Chen, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/510,033

(22) Filed: Feb. 22, 2000

(51) Int. Cl.[7] .................................................. A61F 2/06
(52) U.S. Cl. ....................................................... 623/1.11
(58) Field of Search ............................... 623/1.11, 1.12, 623/1.13, 1.14, 1.15, 1.16, 1.17, 1.18, 1.19, 1.2, 1.21, 1.22; 606/108, 191, 192, 194, 195, 198

(56) References Cited

U.S. PATENT DOCUMENTS

| | | |
|---|---|---|
| 4,733,665 A | 3/1988 | Palmaz |
| 4,950,227 A | 8/1990 | Savin et al. |
| 5,403,341 A | 4/1995 | Solar ........................... 606/198 |
| 5,470,313 A | 11/1995 | Crocker et al. |
| 5,733,299 A | 3/1998 | Sheiban et al. |
| 5,772,669 A | 6/1998 | Vrba |
| 5,807,327 A | 9/1998 | Green et al. |
| 5,807,404 A | 9/1998 | Richter |
| 5,810,871 A | 9/1998 | Tuckey et al. |
| 5,826,588 A | 10/1998 | Forman |
| 5,836,965 A | 11/1998 | Jendersee et al. |
| 5,846,246 A | 12/1998 | Dirks et al. |
| 5,868,781 A | 2/1999 | Killion |
| 5,913,871 A | 6/1999 | Werneth et al. |
| 5,944,726 A | 8/1999 | Blaeser et al. |
| 5,968,069 A | 10/1999 | Dusbabek et al. |
| 5,971,990 A | 10/1999 | Venturelli |
| 5,980,530 A | 11/1999 | Willard et al. ............... 606/108 |
| 6,004,289 A | 12/1999 | Saab ........................... 604/96 |
| 6,221,097 B1 * | 4/2001 | Wang et al. ................. 606/108 |
| 6,331,186 B1 * | 12/2001 | Wang et al. ................. 623/1.11 |
| 6,395,008 B1 * | 5/2002 | Ellis et al. ................... 606/108 |

FOREIGN PATENT DOCUMENTS

| | | |
|---|---|---|
| EP | 0 770 366 B1 | 7/1996 |
| EP | 0 778 010 A3 | 12/1996 |
| WO | 97/32624 | 9/1997 |

* cited by examiner

*Primary Examiner*—Michael J. Milano
*Assistant Examiner*—Vy Q. Bui
(74) *Attorney, Agent, or Firm*—Vidas, Arrett & Steinkraus PA

(57) ABSTRACT

A stent delivery balloon structure is formed by molding at a desired pressure, temperature and tension a medical balloon with a tube disposed thereabout and subsequently removing one or more layers of material from the body portion of the thus formed medical balloon structure.

14 Claims, 1 Drawing Sheet

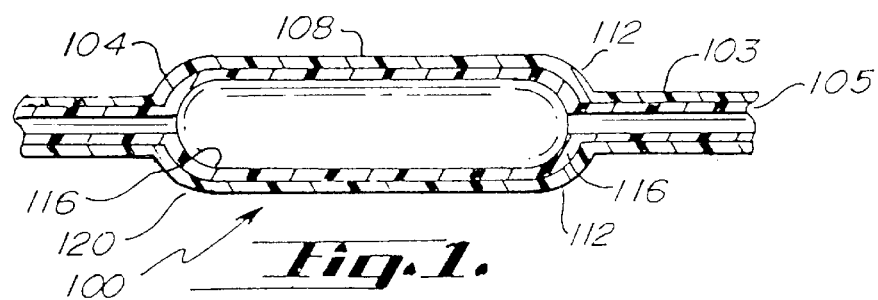
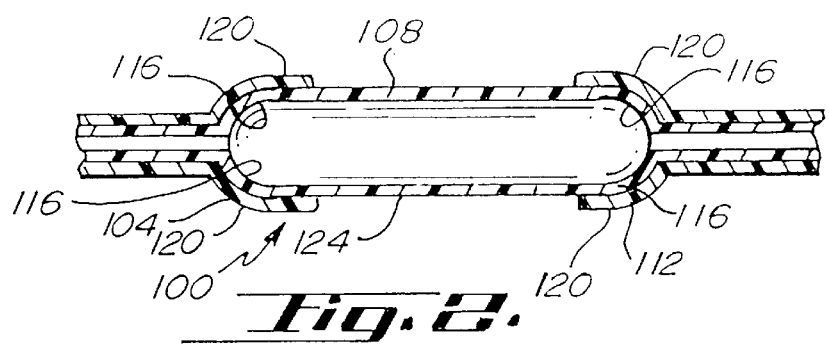
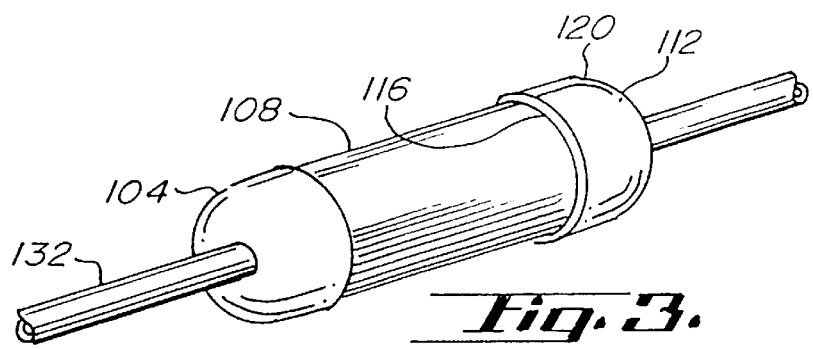
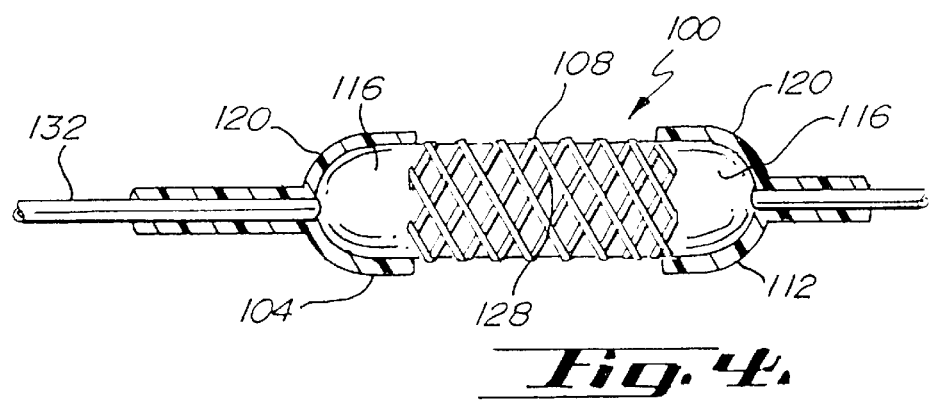

STENT DELIVERY BALLOON WITH SECUREMENT STRUCTURE

BACKGROUND OF THE INVENTION

In typical PTCA procedures, a guiding catheter is percutaneously introduced into the cardiovascular system of a patient through a vessel and advanced therein until the distal end of the catheter is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To help prevent restenosis and strengthen the area, a physician can implant an intravascular prosthesis for maintaining vascular patency inside the artery at the lesion. The intravascular prosthesis or stent is expanded to a larger diameter for placement in the vasculature, often by the balloon portion of the catheter. Examples of balloon expandable stents are provided in U.S. Pat. No. 5,807,404 and U.S. Pat. No. 5,868,781. The stent is delivered on a stent delivery catheter. Examples of stent delivery catheters include those disclosed in U.S. Pat. No. 5,944,726, U.S. Pat. No. 5,772,669 and U.S. Pat. No. 4,733,665.

During the delivery of a balloon expandable stent to a desired bodily location, the stent may move relative to the balloon resulting in a non-uniform expansion of the stent and rendering difficult the accurate deployment of the stent. It is, therefore, desirable, in delivering a balloon expandable stent to a desired bodily location, to secure the stent to the balloon prior to expansion of the balloon and stent. A number of stent securement methods and devices have been proposed. U.S. Pat. No. 5,944,726 discloses several stent securement devices including mounting bodies. U.S. Pat. No. 4,950,227 discloses the use of sleeves disposed over a portion of the proximal and distal ends of a stent.

For the purpose of this disclosure, all U.S. patents and patent applications and all other publications referenced herein are incorporated herein by reference in their entirety.

Without limiting the scope of the invention in any way, the invention is briefly summarized below.

BRIEF SUMMARY OF THE INVENTION

The present invention is directed in one embodiment to a method of forming a medical balloon structure. In accordance with the inventive method, a tube is provided and an inner structure selected from the group consisting of medical balloons and medical balloon tubes is also provided. The tube is disposed about the inner structure. The tube and inner structure are then placed in a balloon mold and a predetermined pressure, tension and temperature are applied to the tube and inner structure so as to form a medical balloon structure. The thus formed medical balloon structure includes a proximal cone portion, a body portion and a distal portion and has an outer wall formed from the tube and an inner wall formed from the inner structure. At least a portion of the outer wall is removed from the body portion of the medical balloon structure. Desirably, the entirety of the outer wall in the region of the body portion is removed.

The invention is also directed to a method of forming medical balloon structures comprising the steps of providing an inner structure selected from the group consisting of medical balloons and medical balloon tubes and a plurality of tubes disposed in layers about the inner structure and placing the inner structure and tubes in a mold. The inner structure and plurality of tubes are then molded at a predetermined pressure, tension and temperature so as to form a medical balloon structure having proximal and distal cone portions and a body portion. Subsequent to molding, a desired number of layers of tube are removed from the body portion of the medical balloon structure.

The invention is also directed to medical balloons formed in accordance with the inventive methods. In particular, the invention is directed to a medical balloon structure having been formed of an inner structure selected from the group consisting of medical balloons and medical balloon tubes and a tube disposed thereabout. The inner structure and tube are molded to form a medical balloon structure having proximal and distal cone portions and a body portion. At this stage, the tube forms the outer wall of the medical balloon structure and the inner structure forms the inner wall of the medical balloon structure. A portion of the outer wall, desirably, the entirety of the outer wall, is then removed from the body portion of the medical balloon structure to form the inventive medical balloon structure.

The invention is also directed to medical balloon structures formed from an inner structure selected from the group consisting of medical balloons and medical balloon tubes and a plurality of tubes disposed in layers about the inner structure. The inner structure and plurality of tubes are molded so as to form a medical balloon structure having proximal and distal cone portions and a body portion. Subsequent to molding, a desired number of layers of tube are removed from the body portion of the medical balloon structure.

In yet another embodiment, the invention is directed to a medical balloon structure comprising a proximal cone portion, a distal cone portion and a body portion. The proximal cone portion, distal cone portion and body portion each have a number of layers of material. At least a portion of the body portion has fewer layers of material than at least one of the proximal and distal cones.

The invention is further directed to catheters comprising the inventive medical balloons. One such catheter is a stent delivery catheter employing an inventive balloon. Desirably, at least one outer layer of the proximal and distal cone sections will be moved toward one another and reside over portions of the proximal and distal ends of the stent.

In another aspect, the invention is directed to a method for fastening a stent to a catheter in a manner suitable for introduction, and later release, of the stent to a body cavity. The method includes the steps of (a) providing a catheter having an inventive medical balloon structure as disclosed above disposed about a distal portion thereof; (b) providing a stent having a contracted and an expanded condition; (c)

disposing the stent about the body portion of the medical balloon structure; and (d) pulling a portion of the proximal and distal cones toward one another so that a portion of the proximal cone is disposed over a proximal portion of the stent and a portion of the distal cone is disposed over of a distal portion of the stent thereby fixing the stent to the catheter when the stent and medical balloon structure are in their contracted state or condition.

In yet another aspect of the invention, the invention features a method for positioning a stent within a body cavity, including the steps of (a) providing a stent delivery system with an inventive medical balloon structure and stent secured thereto; (b) introducing the stent delivery system into the body cavity; (c) causing the medical balloon structure to expand and thereby simultaneously expanding the stent and causing the portions of the cone section which overlie the proximal and distal portions of the stent to be released from their position overlying the stent, at least partially contracting the catheter, and (d) removing the catheter from the body cavity by axially pulling the catheter from the body cavity.

BRIEF DESCRIPTION OF THE SEVERAL VIEWS OF THE DRAWING(S)

FIG. 1 shows a side elevational view of a medical balloon structure prior to removal of materials from the body portion.

FIG. 2 shows a side elevational view of the medical balloon structure of FIG. 1 following removal of material from the body portion.

FIG. 3 shows a perspective view of the medical balloon structure shown in FIG. 2.

FIG. 4 shows a side elevational view of a portion of an inventive medical balloon structure with a stent disposed thereon, the balloon structure mounted on a stent delivery catheter.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, the term stent refers to stents, stentrafts, grafts and other endoluminal prostheses.

In one embodiment, the invention is directed to a method of forming an inventive medical balloon structure. In accordance with the method, an inner structure in the form of a medical balloon is provided and a tube is provided. The tube is disposed about the balloon and the tube and medical balloon placed in a balloon mold. In accordance with well known balloon production methodology, a predetermined pressure, tension and temperature are applied to the tube and balloon in the mold so as to form a medical balloon structure. The resulting medical balloon structure, shown generally at 100 in FIG. 1, includes a proximal cone portion 104, a body portion 108 and a distal portion 112. An outer wall 103 of the medical balloon structure is formed from the tube and an inner wall 105 of the balloon structure is formed from the medical balloon. As shown in FIGS. 2 and 3, at least a portion of the outer wall is removed from the body portion 108 of the medical balloon structure. The entire portion of the outer wall may be removed from body portion 108 of balloon structure 100 but desirably, a short length of outer wall will remain adjacent to the cones, as shown in FIG. 2. The exact amount of outer wall remaining in the body portion adjacent to the cones will depend on the intended use of the balloon.

In another embodiment of the invention, an inner structure in the form of a medical balloon tube is provided and a second tube is provided. The tube is disposed about the balloon tube and the tube and medical balloon tube placed in a balloon mold. In accordance with well known balloon production methodology, a predetermined pressure, tension and temperature are applied to the tube and balloon tube in the mold so as to form a medical balloon structure. Subsequent to molding, a desired amount of balloon material is removed from the body portion of the medical balloon structure.

The invention is also directed to a method of forming a medical balloon structure comprising the steps of providing a medical balloon or a medical balloon tube and a plurality of tubes disposed in layers about the medical balloon or medical balloon tube and placing the balloon (or balloon tube) and tubes in a mold. The medical balloon (or balloon tube) and plurality of tubes are then molded at a predetermined pressure, tension and temperature so as to form a medical balloon structure having proximal and distal cone portions and a body portion. Subsequent to molding, a desired number of layers of tube are removed from the body portion of the medical balloon structure.

The materials removal step may be accomplished using any of a number of material removal techniques include mechanical, chemical or laser. Mechanical means for removal of the outer layer(s) include mechanical trimming, skiving and grinding. A suitable grinding process is described in commonly assigned U.S. application Ser. No. 09/401618 filed Sep. 22, 1999. The outer layer(s) may also be removed by masking suitable portions of the balloon and chemically etching the balloon or by laser ablation of the layer(s) from the body portion. A suitable process for laser ablation is disclosed in U.S. Pat. No. 5,826,588 to Forman.

The invention is also directed to inventive balloons formed in accordance with the inventive methods disclosed herein.

The invention is also directed to a medical balloon structure whose body portion and cone portions are comprised of a predetermined number of layers of material. The number of layers of material in the cone sections differs from the number of layers of material in the body section. Desirably, the number of layers of material in the cone section will exceed the number of layers of material in the body portion of the balloon structure.

In one embodiment of the invention, as shown in FIGS. 2 and 3, a medical balloon structure shown generally at 100 includes a proximal cone portion 104, a body portion 108 and a distal cone portion 112. Proximal cone portion 104 and distal cone portion 112 are each formed of two layers of material. Each cone portion has an inner wall 116 and an outer wall 120. Body portion 108 consists of a single layer of material 124.

The proximal and distal cone sections may comprise additional layers, as may the body portion, as long as the number of layers of the cones exceeds the number of layers of the body section.

In yet another embodiment, the invention is directed to a medical balloon structure comprising a proximal cone portion, a distal cone portion and a body portion. The proximal cone portion, distal cone portion and body portion each have a number of layers of material. At least a portion of the body portion has fewer layers of material than at least one of the proximal and distal cones. The proximal and distal cone portions may have a like number of layers or a different number of layers. Where the proximal and distal cone portions have a different number of layers, the difference in the number of layers may be achieved by removing layers of material from at least one of the proximal and cone portions. One such balloon may have a few number of layers of material in the proximal cone portion to allow for improved trackability of the balloon.

The inventive balloons may be used for a variety of purposes. They are especially useful as expansion means in stent delivery catheters. A medical balloon structure for use in stent delivery is shown in FIG. 4. Medical balloon structure 100, similar to that shown in FIG. 2, is mounted on the distal end of catheter 132. Although not shown, catheter 132 includes an inflation lumen in fluid communication with medical balloon 100. Stent 128 is disposed about body portion 108 of medical balloon structure 100. Desirably, as shown in FIG. 4, outer walls 120 of the proximal 104 and distal cone portions 112 are pulled toward one another to cover a portion of the proximal and distal ends of stent 128 and aid in stent retention.

Where the balloon structure is formed of a plurality of tubes, it is desirable to remove a sufficient number of layers from the body portion so as to form a recessed portion in which the stent may reside.

More generally, in the case of a balloon for expansion of a stent, regardless of how many layers of material are used in the formation of the inventive balloon, sufficient material should be removed so as to form a recessed portion in which the stent may reside. Desirably, sufficient balloon material should be removed so that portions of the balloon adjacent to the recess will extend to at least 50% and more desirably 75% of the height of a stent (unexpanded) which is disposed in the recess. Even more desirably, sufficient balloon material should be removed so that the portions of the balloon adjacent to the recess will extend above a stent (unexpanded) disposed in the recess. To that end, the inventive balloons may be made prepared by removing a predetermined amount of material from the body portion of the stent, the amount of material to be determined on the basis of the inner and outer diameters of the unexpanded stent to be disposed in the thus formed recess.

Also, in the case of a balloon for expansion of a stent, the axial length of the recess which is formed by removal of material from the body portion of the balloon should correspond to the length of the stent to be disposed in the recess or be slightly longer.

The invention is further directed to catheters comprising the inventive balloons disclosed herein. In one embodiment, the invention is directed to a stent delivery catheter comprising an inventive balloon disposed thereon and a stent disposed on the balloon. Desirably, the proximal and distal portions of the stent will have a portion of the proximal and distal cones pulled thereover, as shown in FIG. 4, to aid in stent retention. The inventive balloons may be used in conjunction with virtually any stent delivery catheter configured for balloon expansion of the stent.

In another aspect, the invention is directed to a method for fastening a stent to a catheter in a manner suitable for introduction, and later release, of the stent to a body cavity. The method includes the steps of (a) providing a catheter having an inventive medical balloon structure as disclosed above disposed about a distal portion thereof; (b) providing a stent having a contracted and an expanded condition; (c) disposing the stent about the body portion of the medical balloon structure; and (d) pulling a portion of the proximal and distal cones toward one another so that a portion of the proximal cone is disposed over a proximal portion of the stent and a portion of the distal cone is disposed over of a distal portion of the stent thereby fixing the stent to the catheter when the stent and medical balloon structure are in their contracted state or condition.

In yet another aspect of the invention, the invention features a method for positioning a stent within a body cavity, including the steps of (a) providing a stent delivery system with an inventive medical balloon structure and stent secured thereto, as described above; (b) introducing the stent delivery system into the body cavity; (c) causing the medical balloon structure to expand and thereby simultaneously expanding the stent and causing the portions of the cone section which overlie the proximal and distal portions of the stent to be released from their position overlying the stent, at least partially contracting the catheter, and (d) removing the catheter from the body cavity by axially pulling the catheter from the body cavity.

The medical balloon and tubes for use in the practice of the inventive method is desirably formed from a material selected from the group consisting of non-compliant balloon materials, semi-compliant balloon materials and combinations thereof. Suitable non-compliant and semi-compliant materials include polyethyleneterephthalate (PET), high density polyethylene, polyamides, polycarbonates, Nylon, polyurethanes, polyvinyl chloride, ethylene-vinyl acetate copolymers, and mixtures and combinations thereof. Other suitable materials include thermoplastic elastomers i.e. block copolymers; copolymers and terpolymers of ethylene; homopolymers, copolymers and terpolymers of propylene; ethylene a-olefins; polyesters; vinyl copolymers; ionomer materials and so forth. More specifically, materials such as Selar®, polyether-polyester block copolymers (i.e. Hytrel® from DuPont or Arnitel® from DSM, Netherlands), Pebax® (polyether block amide copolymers), Surlyn®, polytetrafluoroethylene, polyetherurethanes, polyesterurethanes, polyurethane ureas, polyurethane siloxane block copolymers, silicone polycarbonate copolymers, acrylonitrile-butadiene-styrene copolymers; polyphenylene sulfides; copolyesters or other similar extrudable thermoplastic, polymeric materials, or composites thereof may be utilized in the present invention.

Desirably, the inventive medical balloon structure will have a soft outer layer. Also desirably, the medical balloon or medical balloon tube will be made of a material which is harder than the tubing material. To that end, a medical balloon or medical balloon tube may be inserted into a soft and lower durometer thermoplastic elastomer tubing in order to form the inventive medical balloon structure.

In addition to the specific embodiments claimed below, the invention is also directed to other embodiments having any other possible combination of the dependent features claimed below.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claim is:

1. A medical balloon structure comprising:
   a proximal cone portion;
   a distal cone portion;
   a body portion;
   the proximal cone portion having at least two layers of material;
   the distal cone portion having a number of layers of material; and
   the body portion having a number of layers of material, wherein at least a portion of the body portion has fewer layers of material than at least one of the proximal and distal cones, wherein the at least two layers of material are blow molded together and the number of layers of material of the distal cone portion are blow molded together.

2. The medical balloon structure of claim 1 wherein the proximal and distal cone portions are formed of the same number of layers of material.

3. The medical balloon structure of claim 2, proximal and distal cone portions having an outer wall and an inner wall, the body portion having only an inner wall, wherein
   the outer wall of the proximal cone portion and the outer wall of the distal cone portion were formed of a single tube,
   the inner wall of the medical balloon structure was formed of an inner structure selected from the group consisting of medical balloons and medical balloon tubes,
   the inner structure and tube were molded, at least a portion of the tube overlying the body portion having been removed subsequent to molding.

4. The medical balloon structure of claim 3 wherein the proximal and distal cone outer walls are made of a material softer than the material from which the inner structure is made.

5. The medical balloon structure of claim 3 wherein the inner structure is formed of a material selected from the group consisting of compliant balloon materials, semi-compliant balloon materials and combinations thereof.

6. The medical balloon structure of claim 3 wherein the tube is formed of a thermoplastic elastomer.

7. The medical balloon structure of claim 3 wherein:
   the proximal and distal cone outer walls are made of a material softer than the material from which the inner structure is made,
   the inner structure is formed of a material selected from the group consisting of compliant balloon materials, semi-compliant balloon materials and combinations thereof, and
   the tube is formed of a thermoplastic elastomer.

8. A catheter including a medical balloon structure as in claim 2 disposed thereon.

9. A catheter including a medical balloon structure as in claim 7 disposed thereon.

10. A stent delivery catheter including a medical balloon structure as in claim 7 disposed thereon and a stent disposed about the body portion of the balloon structure.

11. The medical balloon structure of claim 3 wherein the inner structure is a medical balloon.

12. The medical balloon structure of claim 3 wherein the inner structure is a medical balloon tube.

13. The medical balloon structure of claim 2 wherein the portion of the body portion having fewer layers of material than the proximal and distal cones forms a recess sized to receive an unexpanded stent.

14. The medical balloon structure of claim 13 with a stent received in the recess.

* * * * *